United States Patent
Kobayashi et al.

(10) Patent No.: US 10,179,251 B2
(45) Date of Patent: Jan. 15, 2019

(54) THERAPEUTIC DEVICE AND A METHOD OF DRIVING THE THERAPEUTIC DEVICE

(71) Applicant: KABUSHIKI KAISHA TOSHIBA, Minato-Ku (JP)

(72) Inventors: Hideo Kobayashi, Ota (JP); Kiyohiko Kitagawa, Yokohama (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 15/699,776

(22) Filed: Sep. 8, 2017

(65) Prior Publication Data
US 2018/0064958 A1    Mar. 8, 2018

(30) Foreign Application Priority Data

Sep. 8, 2016  (JP) ................................ 2016-175778

(51) Int. Cl.
*A61N 5/10*    (2006.01)

(52) U.S. Cl.
CPC .... *A61N 5/1081* (2013.01); *A61N 2005/1085* (2013.01); *A61N 2005/1087* (2013.01)

(58) Field of Classification Search
CPC ........ A61N 5/10; A61N 5/103; A61N 5/1064; A61N 5/1065; A61N 5/1077; A61N 5/1078; A61N 5/1081; A61N 2005/1085; A61N 2005/1087; G21K 5/00; G21K 5/02; G21K 5/04; G21K 5/06; G21K 5/08; G21K 5/10
See application file for complete search history.

(56) References Cited

U.S. PATENT DOCUMENTS

| 5,993,373 A * | 11/1999 | Nonaka .................... A61N 5/10 250/492.1 |
| 6,803,591 B2 * | 10/2004 | Muramatsu .............. A61N 5/10 250/397 |
| 8,368,043 B2 * | 2/2013 | Havelange ........... A61N 5/1081 250/454.11 |
| 2017/0001041 A1 * | 1/2017 | Yamashita ........... A61N 5/1049 |

FOREIGN PATENT DOCUMENTS

| CN | 102026681 A | 4/2011 |
| JP | 52-034862 A | 3/1977 |
| JP | 11-47287 A | 2/1999 |
| JP | 2001-129103 A | 5/2001 |
| JP | 2001-353228 A | 12/2001 |
| JP | 2011-156263 A | 8/2011 |
| WO | WO 2006/060886 A1 | 6/2006 |

* cited by examiner

*Primary Examiner* — David E Smith
(74) *Attorney, Agent, or Firm* — Oblon, McClelland, Maier & Neustadt, L.L.P.

(57) ABSTRACT

A therapeutic device is provided, including a cylindrical gantry; a pedestal, a particle beam irradiation device, a first rail, and a second rail all disposed in the gantry; the first rail including an arc-shaped portion and a straight portion, the second rail having a same shape as the first rail, a rail motor on the second rail to rotate the second rail in a opposite direction than that of the gantry, first and second moving floors on the rails and respectively including first floor panels rotatably connected to each other and second floor panels rotatably connected to each other, a first end panel of the first floor and a fourth end panel of the second floor being detachably connected to the irradiation device, and a second end panel of the first floor being detachably connected to a third end panel of the second floor.

10 Claims, 4 Drawing Sheets

THERAPEUTIC DEVICE AND A METHOD OF DRIVING THE THERAPEUTIC DEVICE

CROSS-REFERENCE TO RELATED APPLICATION

The present application is based on and claims priority to Japanese Patent Application No. JP 2016-175778, filed Sep. 8, 2016, the entire contents of which are incorporated herein by reference.

BACKGROUND

Field

Embodiments relate to a particle beam therapy device with a gantry and methods of operating the device.

Description of Related Art

One of the ways to treat a patient's cancer is by irradiating an affected area including the cancer with a particle beam. Such treatment may be performed by a therapeutic device including a particle beam irradiation device. The therapeutic device includes a cylindrical gantry having a pedestal in its inner space and a particle beam irradiation device fixed in the inner wall of the gantry. The inside of the gantry includes a treatment room. A patient lies on the pedestal. The particle beam irradiation device moves around the patient by the gantry rotating and the patient's cancer is irradiated with the particle beam. The desired position and focus of the particle beam is adjusted by rotating the gantry and by moving the position of the pedestal.

It is desired that the floor of the treatment room should always remain flat in the cylindrical gantry so that the patient may remain calm, and so that health care workers can conveniently access the patient inside of the gantry.

SUMMARY

Present embodiments disclose a therapeutic device including a cylindrical gantry having an inner space and an inner surface, a pedestal disposed in the inner space, a particle beam irradiation device disposed in the inner surface and being configured to emit a particle beam toward the pedestal, a first rail disposed in the gantry and comprising a first arc-shaped portion and a first straight portion, ends of the first arc-shaped portion being connected to respective ends of the first straight portion, a second rail disposed in the gantry and comprising a second arc shaped portion and a second straight portion, ends of the second arc-shaped portion being connected to respective ends of the second straight portion, the second arc-shaped portion extending along an inner periphery of the gantry, a rail motor attached to the second rail and being configured to rotate the second rail in a direction opposite to a rotation direction of the gantry, a first moving floor disposed on the first rail and on the second rail, and comprising a plurality of first floor panels rotatably connected to each other, and a second moving floor disposed on the first rail and on the second rail, and comprising a plurality of second floor panels rotatably connected to each other, wherein a first end panel of the first moving floor is detachably connected to the particle beam irradiation device, the second end panel of the first moving floor is detachably connected to a third end panel of the second moving floor, and a fourth end panel of the second moving floor is detachably connected to the particle beam irradiation device.

Present embodiments disclose a method of operating the therapeutic device including positioning the first moving floor and the second moving floor so as to not contact the particle beam irradiation device, rotating the gantry in the rotation direction, rotating the second rail in the direction opposite to the rotation direction of the gantry during the rotating of the gantry, moving at least one of the first moving floor and the second moving floor on the first rail while maintaining a predetermined distance from the particle beam irradiation device during or after the rotating of the gantry, and further moving at least one of the first moving floor and the second moving floor after the rotating of the gantry.

Present embodiments disclose a method of operating the therapeutic device including positioning the first moving floor and the second moving floor so as to not contact the particle beam irradiation device, rotating the gantry in the rotation direction, rotating the second rail in the direction opposite to the rotation direction of the gantry during the rotating of the gantry, moving at least one of the first moving floor and the second moving floor on the first rail while maintaining a predetermined distance from the particle beam irradiation device during or after the rotating of the gantry and further moving at least one of the first moving floor and the second moving floor after the rotating of the gantry, wherein the further moving of said at least one of the first moving floor and the second moving floor are controlled by the first detector and the second detector.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein.

DETAILED DESCRIPTION

Figure 1:
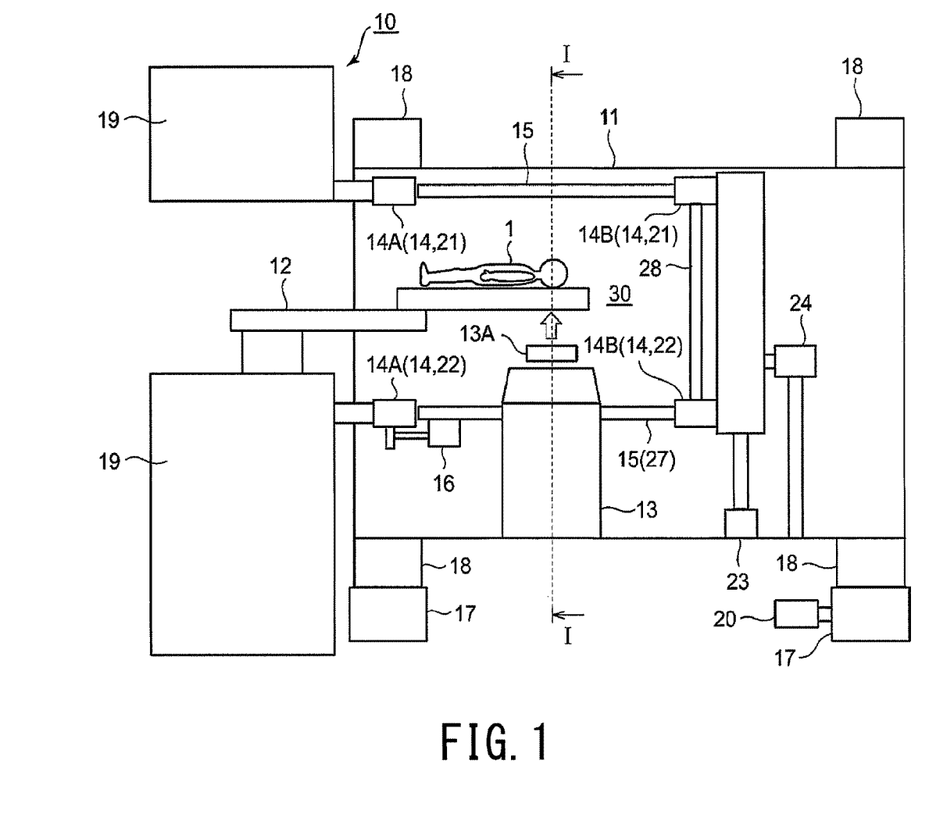
FIG. 1 is a schematic sectional view of a therapeutic device according to an embodiment.
Figure 2:
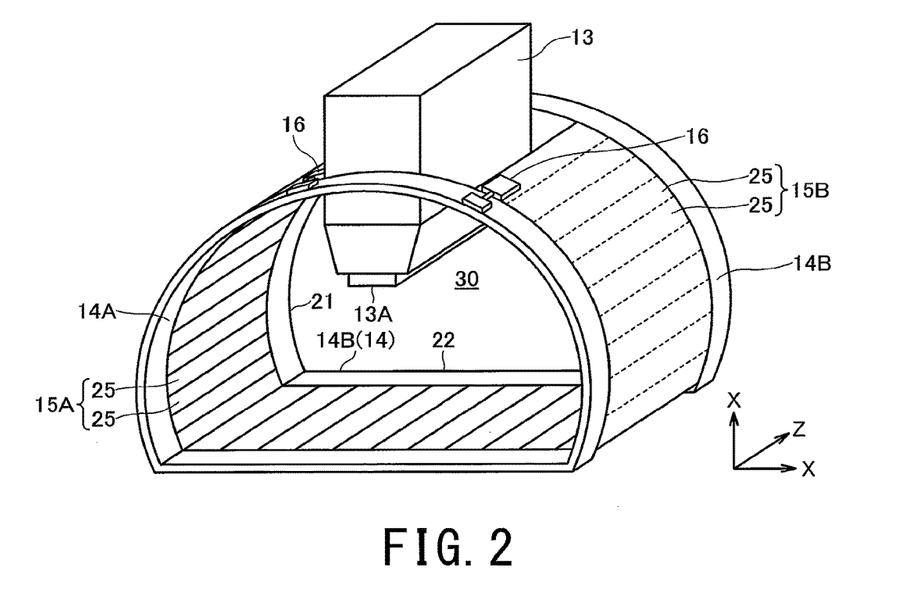
FIG. 2 is a perspective view of a portion of the therapeutic device of FIG. 1, according to an embodiment.

Hereafter, embodiments are described with reference to the drawings. An overview of a particle beam therapy device is described with reference to FIGS. 1-7. FIG. 2 is a perspective view of a portion of the therapeutic device of FIG. 1, showing moving floors according to an embodiment. FIGS. 3-7 are schematic sectional views of the therapeutic device of FIG. 1, taken along line I-I and depicting various gantry rotation angles, according to an embodiment.

The particle beam therapeutic device shown in FIGS. 1-7 may irradiate a portion of the patient on the pedestal with a particle beam oriented in any direction. The particle beam therapeutic device 10 includes a pedestal 12, a gantry 11, a particle beam irradiation device 13, first and second rails 14A, 14B, and first and second moving floors 15A, 15B.

The gantry 11 is cylindrical and the central axis of the gantry 11 is horizontal relative to a floor of the room where the gantry 11 is disposed. End rings 18 are attached to both the ends of the gantry 11. Supporting rollers 17 contact the end rings 18. The gantry 11 is supported by supporting roller 17 through the end rings 18. The supporting rollers 17 are derived by supporting roller motor 20. The supporting roller motor 20 drives the supporting rollers 17 and the gantry 11 rotates around its central axis.

The pedestal 12 is fixed on a platform 19 holding the gantry 11. The pedestal 12 does not rotate with the gantry 11. Patient 1 can lie on the pedestal 12. The pedestal 12 is movable in directions parallel to the central axis of the gantry 11. For example, pedestal 12 may move into gantry 11 or out from gantry 11.

The particle beam irradiation device 13 is provided on the inner wall of the gantry 11. The particle beam irradiation device 13 rotates with the gantry 11. The gantry 11 rotates from 180° to −180° around the central axis. The particle beam irradiation device 13 includes an irradiation opening 13A. A particle beam may be emitted from the irradiation opening 13A. Rotating the gantry 11 causes the particle beam irradiation device 13 to rotate around the patient 1 on the pedestal 12, and a portion of the patient may be irradiated with the particle beam from any direction in 360° around the pedestal. As shown in FIGS. 3-7, junction 13B represents points where the particle beam irradiation device 13 is fixed on the inner wall of the gantry 11.

The pedestal 12 is also in the treatment room 30 and is movable into and out of the gantry 11. The treatment room 30 includes the first and the second moving floors 15A, 15B. The first and the second moving floors 15A, 15B each include a plurality of floor panels 25 connected each other. For example, the floor panels 25 are connected to each other with hinges. Each floor panel 25 can pivot at the hinge connecting it to another floor panel 25. Each floor panel 25 is rectangular, with a long side thereof being oriented parallel to the central axis of the gantry 11. The floor panels 25 are connected to each other along the long sides thereof. The first and the second moving floors 15A, 15B therefore behave as a single plate and can bend due to the connected floor panels 25.

Each of the first moving floor 15A and the second moving floor 15B is provided on the first rail 14A and on the second rail 14B, and moves on the first rail 14A and the second rail 14B. The shape of the first rail 14A includes an arc-shaped portion 21 and a straight portion 22, ends of the arc-shaped portion being smoothly connected to respective ends of the straight portion. Similarly, the shape of the second rail 14B includes an arc-shaped portion 21 and a straight portion 22, ends of the arc-shaped portion being smoothly connected to respective ends of the straight portion.

The first rail 14A is provided at an end of the gantry 11. The first rail 14A is fixed on the platform 19 holding the gantry 11. The straight portion 22 of the first rail 14A is horizontal relative to the floor of treatment room 30 and is located in a lower portion of the interior of the gantry 11. The arc-shaped portion 21 is located along an inner periphery of the gantry 11 above the straight portion 22. The first rail 14A does not rotate.

The second rail 14B is provided at the other end of the gantry 11. The second rail 14B is held in the gantry 11 by a rail supporting member 23. The second rail 14B is rotated by a rail rotating motor 24. For example, the rail supporting member 23 and the rail rotating motor 24 are provided on the inner side of the gantry 11. The rail rotating motor 24 rotates the second rail 14B. The rotation of the second rail 14B is synchronized with the rotation of gantry 11 and may be counterclockwise relative to the clockwise rotation of the gantry 11. Such rotation of the second rail 14B keeps the straight portion 22 of the second rail 14B horizontal and at a lower position than the arc-shaped portion 21. The first rail 14A and the second rail 14B are stationary regardless of the rotation of the gantry 11.

A back panel 28 is provided on the second rail 14B. The back panel 28 is disposed in a plane that is perpendicular to the central axis of the gantry 11. On the first rail 14A, a total length of the first moving floor 15A and the second moving floor 15B is longer than a length of the straight portion 22. The particle beam irradiation device 13 is disposed between the first moving floor 15A and the second moving floor 15B. A total length of the first moving floor 15A, the particle beam irradiation device 13, and the second moving floor 15B is shorter than a length of the circumference of the first rail 14A.

In the treatment room 30, the first moving floor 15A, the second moving floor 15B, a part of inner surface of the gantry 11, and the back panel 28 are disposed. A cross section of the treatment room 30 perpendicular to the central axis of the gantry 11 consists of an arc-shaped part and a straight part connected smoothly at both ends thereof.

In the treatment room 30, there is a flat and a horizontal floor composed by the first moving floor 15A and/or the second moving floor 15B. The flat part of the moving floors 15A, 15B in the treatment room 30 is called flat floor 27. In the treatment room 30, the arc-shaped part composed by the first and second moving floors 15A, 15B, or the first and second moving floors 15A, 15B, and the inner surface of the gantry is called arc wall 26. The first moving floor 15A and the second moving floor 15B are rigid enough to support several people who may be, for example, a patient, an engineer of the therapeutic device, and a doctor.

The first and the second moving floors 15A, 15B move on the first and second rails 14A, 14B by floor motors 16. For example, the floor motors 16 are provided on the both ends of each of the first and second moving floors 15A, 15B. More than two floor motors 16 may be provided on one of the moving floors.

Figure 3:
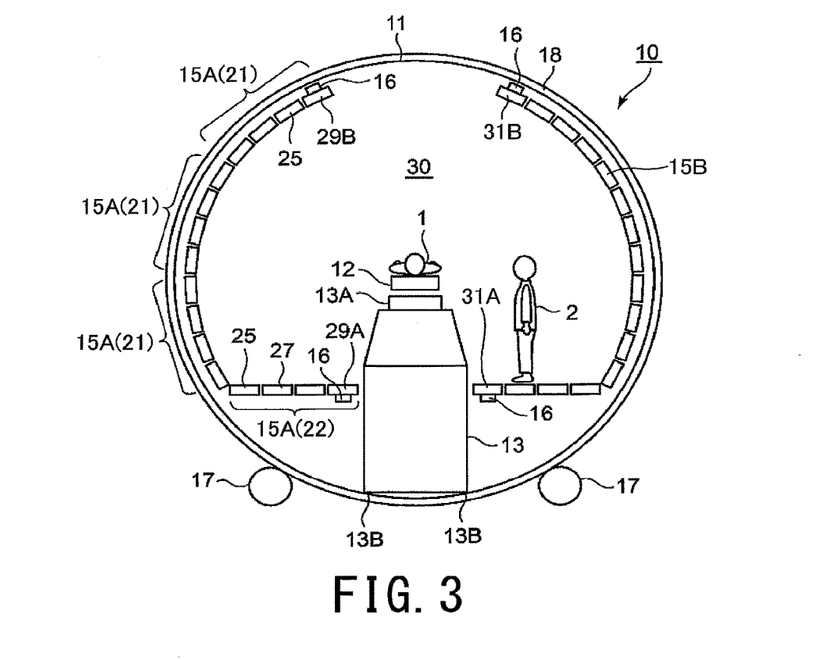
FIG. 3 is a schematic sectional view of the therapeutic device of FIG. 1, taken along line I-I and depicting a gantry rotation angle of 180°, according to an embodiment.

Hereinafter, the operation of the therapeutic device 10 is described. As shown in FIG. 3, for example, particle beam irradiation device 13 is movable by the gantry 11 rotating around the patient 1 on the pedestal 12. Before the gantry rotates, people on the moving floor exit the treatment room 30 for safety. The patient 1 may remain on the pedestal 12 before and during the gantry rotating. Also, before the gantry rotating, the first moving floor 15A and the second moving floor 15B move to positions where the moving floors 15A, 15B do not contact the particle beam irradiation device 13 that is going to move. The first moving floor 15A and the second moving floor 15B are moved by the floor motors 16.

During rotation of the gantry 11, the moving floors 15A, 14B respectively maintain positions where the moving floors 15A, 15B do not contact the particle beam irradiation device 13, which is also moving. Also, for example, during the rotation of the gantry, the moving floors 15A, 15B may move while maintaining a predetermined distance from the particle beam irradiation device 13.

After the gantry 11 has stopped rotating, the first moving floor 15A continues moving so as to contact its end with the particle beam irradiation device 13. And, the second moving floor 14B moves to contact its end with the particle beam irradiation device 13, also after the gantry 11 has stopped rotating. Moving of the first moving floor 15A and the second moving floor 15B is controlled according to movement of the particle beam irradiation device 13 in a predetermined sequence. Or, moving of the first moving floor 15A and the second moving floor 14B is controlled by an operator observing positions of the moving floors 15A, 15B and of the particle beam irradiation device 13.

As shown in FIG. 3, the floor motors 16 may be attached on both ends of the first moving floor 15A and on both ends of the second moving floor 15B. The end floor panel 25 of the first moving floor 15A that is closest to the particle beam irradiation device 13 is the first end panel 29A. The end floor panel 25 of the first moving floor 15A that is closest to the second moving floor 15B is the second end panel 29B. The end floor panel 25 of the second moving floor 15B that is closest to the first moving floor 15A is the third end panel 31B. The end floor panel 25 of the second moving floor 15B that is closest to the particle beam irradiation device 13 is the fourth end panel 31A.

The operation of the each floor motor 16 is not limited. For example, when the moving floors 15A, 15B are moved upward, the floor motors 16 on the second end panel 29B and on the third end panel 31B are the main drivers of the movement of the moving floors 15A, 15B, and the floor motors 16 on the first end panel 29A and the fourth end panel 31A are the supplemental drivers. Or, when the moving floors are moved upward, the floor motors 16 on the first end panel 29A and the fourth end panel 31 A are the main drivers, and the floor motors 16 on the second end panel 29B and the third end panel 31B are the supplemental drivers. Or, the driving power of the floor motors 16 on the second end panel 29B, the third end panel 31B, the first end panel 29A, and the fourth end panel 31A may be linked together.

When the moving floors 15A, 15B are moved in a direction such that the second end panel 29B and the third end panel 31B are moved downward, closer to the floor where the gantry 11 is disposed, the floor motors 16 on the first end panel 29A and the fourth end panel 31A are the main drivers, and the floor motors 16 on the second end panel 29B and the third end panel 31B are the supplemental drivers. Or, when the moving floors are moved downward, the floor motors 16 on the second end panel 29B and the third end panel 31B are the main drivers, and the floor motors 16 on the second end panel 29B and the third end panel 31B are the supplemental drivers. Or, the driving power of the floor motors 16 on the second end panel 29B, the third end panel 31B, the first end panel 29A, and the fourth end panel 31A may be linked together.

For reasons of safety, when a person, for example a health care worker, is in the treatment room 30, the flat floor 27 is needed to be flat and have no clearance between it and the particular beam irradiation device 13, regardless the position of the particle beam irradiation device 13. And, when the particle beam irradiation device 13 is in the straight portion 22 of flat floor 27, contact points of the irradiation device 13 and the moving floors 15A, 15B (i.e., the end of the first end panel 29A, and of the fourth end panel 31A) change according to the rotation angle of the gantry. The relationship between the rotation angle of the gantry 11 and the position of the particle beam irradiation device 13 is described below. Also, the operation of the particle beam irradiation device 13 (or the gantry 11) and the moving floors 15A, 15B are described below.

For example, as shown in FIG. 3, the particle beam irradiation device 13 is in a position underneath the pedestal 12, when the rotation angle of the gantry 11 is at +180°. The particle beam irradiation device 13 is in the flat floor 27. The end of the first end panel 29A and the end of the fourth end panel 31A are in contact with the particle beam irradiation device 13. In a moving direction of the moving floors 15A, 15B, there is no clearance in the flat floor 27, such that it would not be possible to drop an object, such as a tool, or to allow passage of a person's hand or foot, under the moving floors 15A, 15B.

Figure 4:
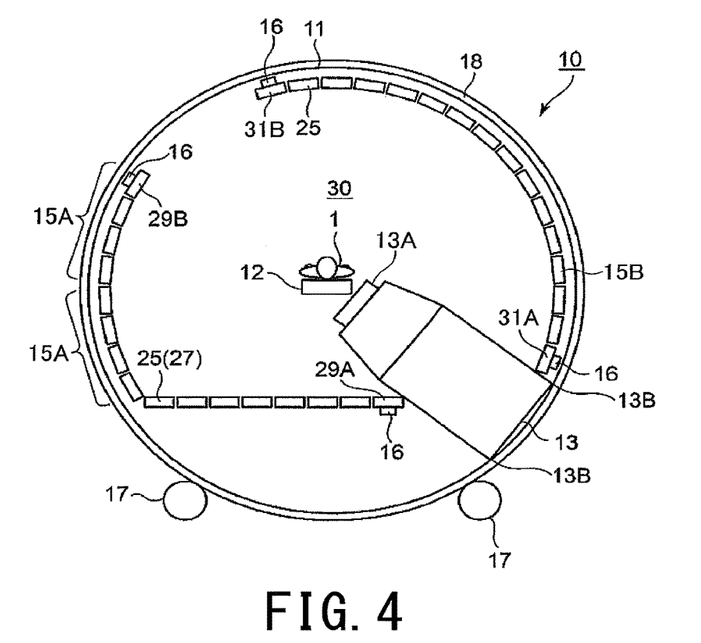
FIG. 4 is a schematic sectional view of the therapeutic device of FIG. 1, taken along line I-I and depicting a gantry rotation angle of 135°, according to an embodiment.

As shown in FIG. 4, the particle beam irradiation device 13 is at a lower diagonal corner position of the pedestal 12, when the rotation angle of the gantry 11 is at +135°. The particle beam irradiation device 13 is still in the flat floor 27 and the length of the flat floor to the left of the particle beam irradiation device 13 is longer than it was when the rotation angle of the gantry 11 is +180°. The position occupied by the particle beam irradiation device 13 and the contact points of the particle beam irradiation device 13 and the moving floors 15A, 15B have changed due to the rotation angle of the gantry 11, but still there is no clearance in the flat floor 27. This is because the moving floors move on the rails after the rotation of the gantry stops in order to contact the end the first end panel 29A and the end the fourth end panel 31A with the particle beam irradiation device 13.

An example of the operation of the gantry rotating from +180° to +135° is described below. The gantry 11 is depicted as rotating in a counterclockwise direction from FIG. 3 to FIG. 4. Before starting the rotation operation, the gantry is at +180° and the particle beam irradiation device 13 is positioned vertically under the pedestal 12. The ends of the first end panel 29A and of the fourth end panel 31A are in contact with the particle beam irradiation device 13. To begin the operation, the second moving floor 15B first moves counterclockwise on the rails to where the end the fourth end panel 31A does not contact the particle beam irradiation device 13 when the gantry is +135°. Second, the gantry rotates to +135°. Then, the first moving floor 15A and the second moving floor 15B move on the rails to contact the ends of the first end panel 29A and of the fourth end panel 31A with the particle beam irradiation device 13.

In another example, the second moving floor 15B moves counterclockwise on the rails to provide a predetermined distance separating the end of the fourth end panel 31A and the particle beam irradiation device 13. This distance may be shorter than the distance to which the particle beam irradiation device 13 will move by the gantry 11 rotating from +180° to +135°. Then, the particle beam irradiation device 13 and the second moving floor 15B move at the same speed to maintain the predetermined distance until the gantry is at +135°. Finally, the first moving floor 15A and the second moving floor 15B move on the rails to contact the ends of the first end panel 29A and of the fourth end panel 31A with the particle beam irradiation device 13.

Figure 5:
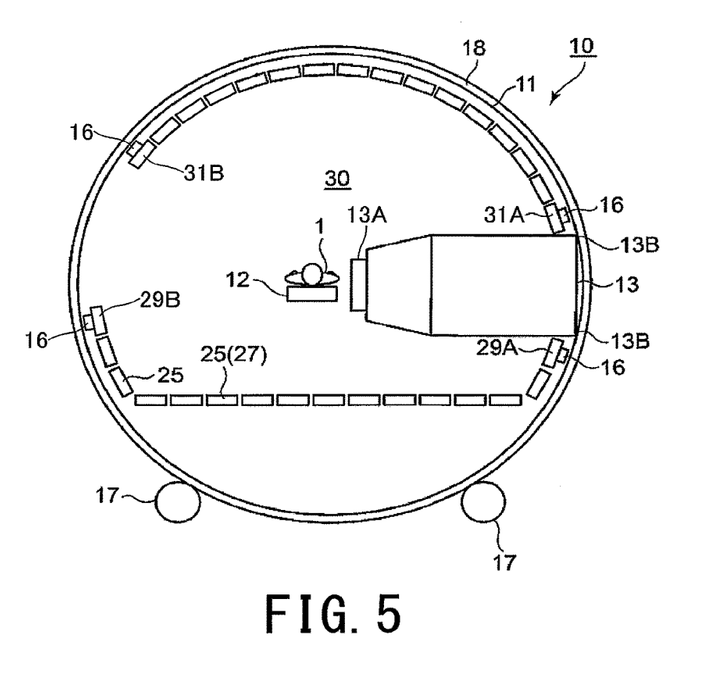
FIG. 5 is a schematic sectional view of the therapeutic device of FIG. 1, taken along line I-I and depicting a gantry rotation angle of 90°, according to an embodiment.

As shown in FIG. 5, the particle beam irradiation device 13 is at a position that is the same height as the pedestal 12, when rotation angle of the gantry 11 is at +90°. The particle beam irradiation device 13 is now along the arc wall 26. There is no clearance in the flat floor 27 because the particle beam irradiation device 13 is no longer disposed in a portion occupied by the flat floor 27. The moving floors 15A, 15B move on the rails after the rotation of the gantry to cover the straight portion 22 with the first moving floor 15A. When the particle beam irradiation device 13 is positioned along the arc wall 26, the contact points 13B of the particle beam irradiation device 13 and moving floors 15A, 15B are stable.

An example of an operation to move the particle beam irradiation device 13 from +135° to +90° is described below. The gantry 11 is depicted as rotating in a counterclockwise direction from FIG. 4 to FIG. 5. Before starting the operation, the gantry is at +135°. The ends the first end panel 29A and of the fourth end panel 31A are in contact with the particle beam irradiation device 13. First, the second moving floor 15B moves counterclockwise on the rails to where the end of the fourth end panel 31A does not contact the particle beam irradiation device 13 when the gantry is at +90°. Second, the gantry rotates to +90°. Then, the first moving floor 15A moves on the rails to cover the straight portion 22 and to contact the end of the first end panel 29A with the particle beam irradiation device 13. At the same time, the second moving floor 15B moves on the rail to contact the end of the fourth end panel 31A with the particle beam irradiation device 13. When the gantry is at +90°, there is no clearance in the flat floor 27 because the particle beam irradiation device 13 is no longer disposed in a portion occupied by the flat floor 27. So, the ends of the first end panel 29A and of the fourth end panel 31A may or may not be in contact with the particle beam irradiation device 13.

Figure 6:
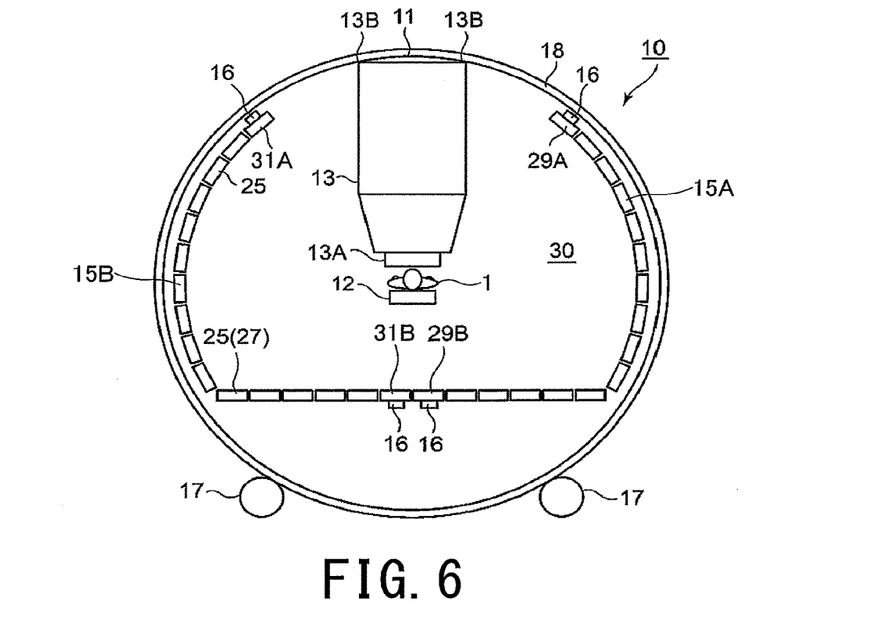
FIG. 6 is a schematic sectional view of the therapeutic device of FIG. 1, taken along line I-I and depicting a gantry rotation angle of 0°, according to an embodiment.

In FIG. 2 and in FIG. 6, the particle beam irradiation device 13 is in a position directly above the pedestal 12, when rotation angle of the gantry 11 is at 0°. The particle beam irradiation device 13 is positioned along the arc wall 26. And, there is no clearance in the flat floor 27 because after the rotation of the gantry the moving floors 15A, 15B move on the rails 14A, 14B to cover the straight portion 22 with floor panels 25. The end of the third end panel 31B contacts the end of the second end panel 29B in the straight portion 22. There is a clearance between the end of the fourth end panel 31A and the particle beam irradiation device 13, and between the end of the first end panel 29A and the particle beam irradiation device 13.

An example of an operation to move the particle beam irradiation device 13 from +90° to 0° is described below. The gantry 11 is depicted as rotating in a counterclockwise direction from FIG. 5 to FIG. 6. First, the second moving floor 15B moves counterclockwise on the rails to provide a predetermined distance between the end of the fourth end panel 31A and the particle beam irradiation device 13. This distance may be shorter than the distance to which the particle beam irradiation device 13 will move by the gantry 11 rotating from +90° to 0°. Then, the particle beam irradiation device 13, the second moving floor 15B, and the first moving floor 15A move at the same speed to maintain the predetermined distance until the gantry is at 0°. Finally, the first moving floor 15A and the second moving floor 15B move on the rails to contact the ends of the second end panel 29B and of the third end panel 31B in the straight portion to form flat floor 27 without clearance therebetween.

As described above, when the particle beam irradiation device 13 is positioned along the arc wall 26, the moving floors 15A, 15B move on the rails 14A, 15B to cover the straight portion 22 without any clearance therebetween. When the particle beam irradiation device 13 is positioned in the flat floor 27, the rotation angle of the gantry 11 is ~+135° to ~+180°, and the moving floors 15A, 15B move on the rails 14A, 15B to contact the first end panel 29A and the third end panel 31B with the particle beam irradiation device 13, in order to not create any clearance in the flat floor 27.

As described above, the relationships of rotation angle of the gantry 11 and position of the particle beam irradiation device 13 are examples. According to the lengths of the arc shaped portion 21 and of the straight portion 22, the relationship of rotation angle of the gantry 11 and position of the particle beam irradiation device 13 is changed. As described above, the gantry 11 rotates from ~+180° to ~0°. But the gantry 11 may also rotate from ~0° to ~−180°. The ~+180° and 0° positions of the gantry 11 and the particle beam irradiation device 13 appear the same. When the gantry 11 rotates from ~0° to ~−180°, there is no clearance in the flat floor 27 due to the contact between the ends of the fourth end panel 31A and of the first end panel 29A with the particle beam irradiation device 13, or due to the contact between the end of the third end panel 31B the end of the second end panel 29B.

The therapeutic device 10 as described above is efficient. For safety reasons, the irradiation device 13 needs to be in contact with the flat floor 27 so as to have no clearance between the irradiation device 13 and the flat floor 27. However, during the gantry 11 rotation from ~+180° to ~+135° (or from ~−135° to ~−180°, the angle of the irradiation device 13 against the straight portion 22 (of flat floor 27) changes according to the rotation angle of the gantry. So, the contact points of the irradiation device 13 and the moving floors 15A, 15B (i.e., the end of the first end panel 29A, and of the fourth end panel 31A) change according to the rotation angle of the gantry.

As shown in FIGS. 3-5 there is no connecting part that connects the irradiation device 13 and the moving floors 15A, 15B. And, the moving floors 15A, 15B can be operated separately from the rotation of the gantry 11 (and of the irradiation device 13). So, consistent with an embodiment, the flat floor 27 with no clearance can be formed regardless of the rotation angle of the gantry 11. Due to the lack of clearance in the flat floor 27, a person may safely and easily approach the pedestal 12.

Ends of the moving floors 15A, 15B can contact the particle beam irradiation device 13. But these ends are not connected with the particle beam irradiation device 13. And, the moving floors 15A, 15B can be controlled independently from the gantry 11 and from the particle beam irradiation device 13. Therefore, parts connecting the moving floors 15A, 15B and the particle beam irradiation device 13 are not necessary. So, the structure of the therapeutic device 10 is simplified. This simplified structure provides increased durability and reduces maintenance costs.

The moving floors 15A, 15B can provide clearance in the flat floor 27 or along arc wall 26 during maintenance of the gantry 11 or of the particle beam irradiation device 13. In other words, the moving floors 15A, 15B being movable by the floor motors 16 makes it easier to access the gantry 11 or the particle beam irradiation device 13 for maintenance.

The moving floors 15A, 15B are independent from the particle beam irradiation device 13. Therefore, there is no extra sound made by parts connecting the moving floors 15A, 15B and the particle beam irradiation device 13. In other words, the therapeutic device 10 is quieter.

There is no need to connect the moving floors 15A, 15B and the particle beam irradiation device 13. The shape of the particle beam irradiation device 13 is not limited by the connecting parts for the moving floors 15A, 15B. Various shapes of the particle beam irradiation device 13 may be considered. For example, a side of the particle beam irradiation device 13 may be tilted, the particle beam irradiation device 13 may be cylindrical, or the particle beam irradiation device 13 may be a relatively short compared to the height depicted in the drawings. Regardless of the shape of the particle beam irradiation device 13, there is no clearance in the flat floor 27 with this therapeutic device 10.

Figure 7:
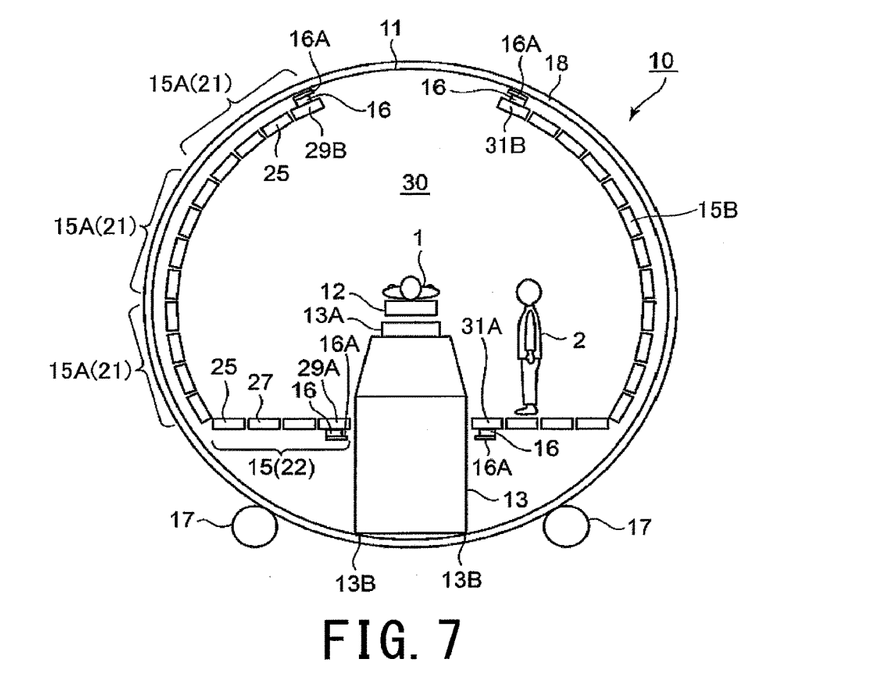
FIG. 7 is a schematic sectional view of the therapeutic device of FIG. 1, taken along line I-I and depicting a gantry rotation angle of −180°, according to an embodiment.

An embodiment of an arranged therapeutic device 10A is described with reference to FIG. 7 below. It is noted that the same configurations as those described above are given the same reference symbols, thereby omitting overlapping description.

In the therapeutic device 10A, sensors 16A measure the distance between the moving floor 15A, 15B and the particle beam irradiation device 13, and may be provided on the moving floors 15A, 15B. The sensors 16A may be provided on the floor motor 16 on the ends of the first end panel 29A and of the fourth end panel 31A. The sensors 16A may be provided on the floor motor 16 on the ends of the second end panel 29B and of the third end panel 31B. The sensors 16A on the ends of the second end panel 29B and of the third end panel 31B measure the distance between the ends of the second end panel 29B and of the third end panel 31B.

The gantry 11 and the moving floors 15A, 15B can be controlled according to the distance measured by the sensors 16A. The gantry 11 and the floors 15A, 15B can be controlled while maintaining a predetermined distance. In other words, the sensors 16A simplify control of the movement of the gantry 11 and the moving floors 15A, 15B.

The sensors 16A are not limited to be on the floor motors 16. The sensors 16A may be on the moving floors 15A, 15B directly. The sensors 16A may be infrared sensors, which detect a distance between the moving floor 15A and the moving floor 15B, or between the moving floors 15A, 15B and the particle beam irradiation device 13. Also, the sensors 16A may be a detector, which can detect a position of the moving floors 15A, 15B, particularly a position of the ends of the moving floors 15A, 15B in the gantry 11 or along the rails 14A, 14B.

Obviously, numerous modifications and variations of the disclosed embodiments are possible in view of the above description. It is therefore to be understood that within the scope of the appended claims, the disclosed embodiments may be practiced otherwise than as specifically described herein.

We claim:

1. A therapeutic device, comprising:
   a cylindrical gantry having an inner space and an inner surface;
   a pedestal disposed in the inner space;
   a particle beam irradiation device disposed in the inner surface and being configured to emit a particle beam toward the pedestal;
   a first rail disposed in the gantry and comprising a first arc-shaped portion and a first straight portion, ends of the first arc-shaped portion being connected to respective ends of the first straight portion;
   a second rail disposed in the gantry and comprising a second arc shaped portion and a second straight portion, ends of the second arc-shaped portion being connected to respective ends of the second straight portion, the second arc-shaped portion extending along an inner periphery of the gantry;
   a rail motor attached to the second rail and being configured to rotate the second rail in a direction opposite to a rotation direction of the gantry;
   a first moving floor disposed on the first rail and on the second rail, and comprising a plurality of first floor panels rotatably connected to each other;
   a second moving floor disposed on the first rail and on the second rail, and comprising a plurality of second floor panels rotatably connected to each other;
   a first detector; and
   a second detector;
   wherein a first end panel of the first moving floor is detachably connected to the particle beam irradiation device, the second end panel of the first moving floor is detachably connected to a third end panel of the second moving floor, a fourth end panel of the second moving floor is detachably connected to the particle beam irradiation device;
   the first detector is configured to determine a first distance between the first end panel and the particle beam irradiation device; and
   the second detector is configured to determine a second distance between the fourth end panel and the particle beam irradiation device.

2. The therapeutic device according to claim 1,
   wherein the first detector is disposed on the first end panel, and
   wherein the second detector is disposed on the fourth end panel.

3. The therapeutic device according to claim 1, further comprising:
   a third detector configured to determine a third distance between the second end panel and the fourth end panel.

4. The therapeutic device according to claim 3,
   wherein the third detector is disposed on the second end panel or the third end panel.

5. The therapeutic device according to claim 3, further comprising:
   a fourth detector configured to determine a position of the first moving floor in the gantry; and
   a fifth detector configured to determine a position of the second moving floor in the gantry.

6. A method of operating the therapeutic device according to claim 1, comprising:
   positioning the first moving floor and the second moving floor so as to not contact the particle beam irradiation device;
   rotating the gantry in the rotation direction;
   rotating the second rail in the direction opposite to the rotation direction of the gantry during the rotating of the gantry;
   moving at least one of the first moving floor and the second moving floor on the first rail while maintaining a predetermined distance from the particle beam irradiation device during or after the rotating of the gantry; and
   further moving at least one of the first moving floor and the second moving floor after the rotating of the gantry.

7. The method of operating the therapeutic device according to claim 6, wherein said at least one of the first moving floor and the second moving floor contacts the particle beam irradiation device after the rotating of the gantry.

8. The method of operating the therapeutic device according to claim 6, further comprising positioning the first moving floor in contact with the second moving floor along the first straight portion of the first rail and along the second straight portion of the second rail when the particle beam irradiation device is positioned above the pedestal in a vertical direction.

9. The method of operating the therapeutic device according to claim 6, wherein the rotating of the gantry, the moving of the first moving floor, and the moving of the second moving floor are each controlled independently.

10. A method of operating the therapeutic device according to claim 1, comprising:
    positioning the first moving floor and the second moving floor so as to not contact the particle beam irradiation device;
    rotating the gantry in the rotation direction;
    rotating the second rail in the direction opposite to the rotation direction of the gantry during the rotating of the gantry;

moving at least one of the first moving floor and the second moving floor on the first rail while maintaining a predetermined distance from the particle beam irradiation device during or after the rotating of the gantry; and
further moving at least one of the first moving floor and the second moving floor after the rotating of the gantry,
wherein the further moving of said at least one of the first moving floor and the second moving floor are controlled by the first detector and the second detector.

* * * * *